United States Patent
Nam et al.

(10) Patent No.: US 11,182,920 B2
(45) Date of Patent: Nov. 23, 2021

(54) AUTOMATED DETERMINATION OF MUSCLE MASS FROM IMAGES

(71) Applicant: Jerry Nam, College Station, TX (US)

(72) Inventors: Jerry Il Nam, College Station, TX (US); Jane Frederick, Chicago, IL (US); Amanda E. Green, Laguna Nigel, CA (US); Cassidy Gobbell, Fort Worth, TX (US); Sarah Hynes, Austin, TX (US); Travis Frankum, Austin, TX (US); Kyle Goebel, Boerne, TX (US); John Paul Hernandez Alcala, Amarillo, TX (US); Mary Julian, Waco, TX (US); Ashley Tucker, Dallas, TX (US)

(73) Assignee: Jerry Nam, College Station, TX (US)

( * ) Notice: Subject to any disclaimer, the term of this patent is extended or adjusted under 35 U.S.C. 154(b) by 190 days.

(21) Appl. No.: 16/396,021

(22) Filed: Apr. 26, 2019

(65) Prior Publication Data

US 2019/0333238 A1  Oct. 31, 2019

Related U.S. Application Data

(60) Provisional application No. 62/663,062, filed on Apr. 26, 2018.

(51) Int. Cl.
*G06T 7/62* (2017.01)
*G06T 7/136* (2017.01)
(Continued)

(52) U.S. Cl.
CPC ............... *G06T 7/62* (2017.01); *A61B 5/055* (2013.01); *A61B 5/201* (2013.01); *A61B 6/032* (2013.01);
(Continued)

(58) Field of Classification Search
None
See application file for complete search history.

(56) References Cited

U.S. PATENT DOCUMENTS

| 5,818,231 A | 10/1998 | Smith |
| 6,123,451 A | 9/2000 | Schaefer et al. |

(Continued)

FOREIGN PATENT DOCUMENTS

| CA | 2967003 A1 | 5/2016 |
| CN | 107146222 A | * 9/2017 |

(Continued)

OTHER PUBLICATIONS

T.M. Maden-Wilkinson et al. "Comparison of MRI and DXA to measure muscle size and age-related atrophy in thigh muscles", J Musculoskelet Neuronal Interact, Sep. 2013, pp. 320-328, 13(3).

(Continued)

*Primary Examiner* — Mohammed Rachedine
(74) *Attorney, Agent, or Firm* — Talem IP Law, LLP

(57) ABSTRACT

Automated determination of muscle mass from images can be carried by performing a thresholding process to an image file to generate a contrasted image, and segmenting pixels of the contrasted image into bone and not bone. The system can distinguish muscle from organ for the pixels segmented as not bone by determining a location of a rib cage of the patient using the pixels segmented as bone, and removing pixels segmented as not bone that are located within the location of the rib cage. The system can calculate a volume of muscle based on remaining pixels segmented as not bone; calculate a total muscle mass based on the volume of muscle; and provide the total muscle mass of the patient. The total muscle mass of the patient can then be used for applications including calculating a glomerular filtration rate.

17 Claims, 11 Drawing Sheets

(51) Int. Cl.
*G06T 7/00* (2017.01)
*G06T 7/11* (2017.01)
*A61B 5/20* (2006.01)
*A61B 5/055* (2006.01)
*A61B 6/03* (2006.01)
*A61B 5/00* (2006.01)
*A61B 5/107* (2006.01)
*A61B 6/00* (2006.01)

(52) U.S. Cl.
CPC .............. *G06T 7/0012* (2013.01); *G06T 7/11* (2017.01); *G06T 7/136* (2017.01); *G06T 2207/10081* (2013.01); *G06T 2207/30012* (2013.01)

(56) References Cited

U.S. PATENT DOCUMENTS

| | | |
|---|---|---|
| 6,198,797 B1 | 3/2001 | Majima et al. |
| 6,233,473 B1 | 5/2001 | Sheperd et al. |
| 6,415,048 B1 | 7/2002 | Schneider |
| 6,442,287 B1 | 8/2002 | Jiang et al. |
| 6,487,445 B1 | 11/2002 | Serita et al. |
| 6,654,445 B2 | 11/2003 | Shepherd et al. |
| 6,816,564 B2 | 11/2004 | Charles, Jr. et al. |
| 6,990,222 B2 | 1/2006 | Arnold |
| 7,116,756 B2 | 10/2006 | Klingenbeck-Regn et al. |
| 7,292,674 B2 | 11/2007 | Lang |
| 7,343,192 B2 | 3/2008 | Reiderman et al. |
| 7,366,559 B2 | 4/2008 | Taicher et al. |
| 7,366,560 B2 | 4/2008 | Taicher et al. |
| 7,545,979 B2 * | 6/2009 | Fidrich ..................... G06T 7/12 382/128 |
| 7,634,119 B2 | 12/2009 | Tsougarakis et al. |
| 7,660,453 B2 | 2/2010 | Lang |
| 7,664,298 B2 | 2/2010 | Lang et al. |
| 7,725,153 B2 | 5/2010 | Kelly et al. |
| 8,295,570 B2 | 10/2012 | Markwardt et al. |
| 8,517,608 B1 | 8/2013 | Arnold |
| 8,554,316 B2 | 10/2013 | Shimizu et al. |
| 8,649,577 B1 * | 2/2014 | Arnold ................... A61B 6/482 382/128 |
| 8,792,689 B2 | 7/2014 | Kelly et al. |
| 8,818,499 B2 | 8/2014 | Karo et al. |
| 9,147,250 B2 | 9/2015 | Liu et al. |
| 9,504,406 B2 | 11/2016 | Chetham et al. |
| 9,767,549 B2 | 9/2017 | Ishikawa et al. |
| 9,865,050 B2 | 1/2018 | Kelly et al. |
| 2003/0216665 A1 | 11/2003 | Masuo et al. |
| 2004/0059242 A1 | 3/2004 | Masuo et al. |
| 2005/0215882 A1 | 9/2005 | Chenevert et al. |
| 2006/0025701 A1 | 2/2006 | Kasahara |
| 2006/0282005 A1 | 12/2006 | Kasahara et al. |
| 2008/0039708 A1 | 2/2008 | Taicher et al. |
| 2009/0245608 A1 * | 10/2009 | Wan .......................... G06T 7/12 382/131 |
| 2009/0262998 A1 * | 10/2009 | Wang ..................... G16H 30/40 382/131 |
| 2011/0142316 A1 | 6/2011 | Wang et al. |
| 2011/0201940 A1 * | 8/2011 | Wang ................. A61K 49/0054 600/476 |
| 2012/0172700 A1 * | 7/2012 | Krishnan ............... G16H 30/20 600/407 |
| 2013/0261470 A1 | 10/2013 | Allison et al. |
| 2014/0039318 A1 | 2/2014 | Zhang et al. |
| 2014/0353486 A1 | 12/2014 | Leonard |
| 2014/0376701 A1 | 12/2014 | Kopperdahl et al. |
| 2018/0049695 A1 | 2/2018 | Hector, Jr. |
| 2018/0052213 A1 | 2/2018 | Romero Gomez et al. |

FOREIGN PATENT DOCUMENTS

| | | | | |
|---|---|---|---|---|
| CN | 108665777 A | * | 10/2018 | |
| JP | 2015167698 A | | 9/2015 | |
| WO | WO-2017222283 A1 | * | 12/2017 | ............... A61B 6/00 |
| WO | WO-2018022866 A1 | * | 2/2018 | ......... C07K 5/06026 |

OTHER PUBLICATIONS

Simon S. Keller et al. "Measurement of brain volume using MRI: software, techniques, choices and prerequisites", Journal of Anthropological Sciences, 2009, pp. 127-151, vol. 87, The Istituto Italiano di Antropologia.
Joel Kullberg, "Assessment of Body Composition Using Magnetic Resonance Imaging", Digital Comprehensive Summaries of Uppsala Dissertations from the Faculty of Medicine 240, 2007, 96 pages.
E. Louise Thomas et al. "Magnetic resonance imaging of total body fat" J. Appl. Physiol., 1998, pp. 1778-1785, 85(5).
Janne West et al. "Precision of MRI-based body composition measurements of postmenopausal women" PLOS One, Feb. 7, 2018, 10 pages.
Steven Heymsfield et al. "Imaging Techniques of Body Composition: Advantages of Measurement and New Uses", Emerging Technologies for Nutrition Research: Potential for Assessing Military Performance Capability, 1997, 29 pages.
"EchoMRI™ Adult Humans Body Composition Analyzer Product Specifications" Retrieved on: Apr. 16, 2018, 2 pages, Retrieved from: http://www.echomri.com/Body_Composition_Humans.aspx.
Debra J Gibson et al. "The role of computed tomography in evaluating body composition and the influence of reduced muscle mass on clinical outcome in abdominal malignancy: a systematic review" European Journal of Clinical Nutrition, Mar. 2015, 25 pages.
Timothy P. Taylor et al. "Glomerular filtration rate can be accurately predicted using lean mass measured by dual-energy X-ray absorptiometry", Nephrol Dial Transplant, Aug. 23, 2005, 4 pages.
Samuel R. Ward et al. "Density and hydration of fresh and fixed human skeletal muscle" Journal of Biomechanics, 2005, pp. 2317-2320.

* cited by examiner

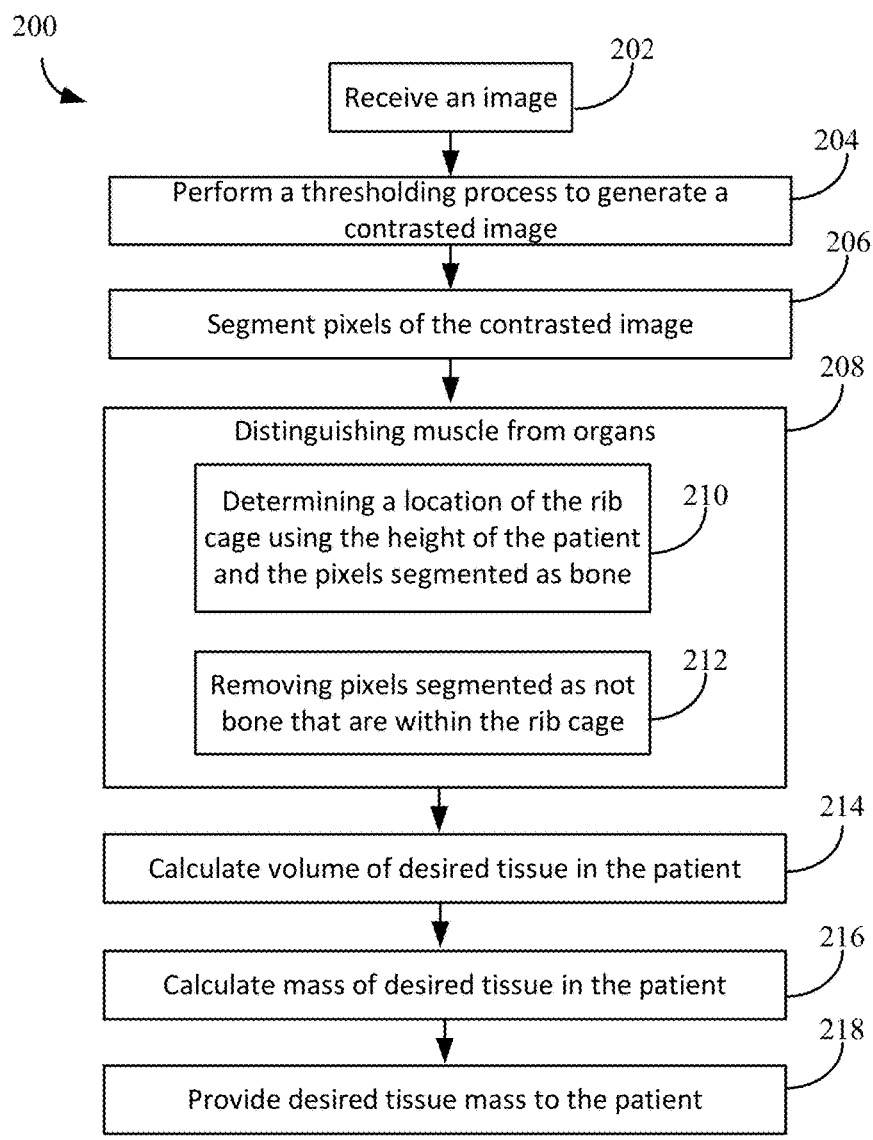

AUTOMATED DETERMINATION OF MUSCLE MASS FROM IMAGES

BACKGROUND

Chronic Kidney Disease (CKD) is present in approximately thirty million American adults in the United States and is the ninth leading cause of death in the United States. Once the kidney is damaged, it cannot be restored. However, if CKD is caught in its earlier stages, health measures can be taken to prevent further damage of the kidneys and stop the progression of the disease before it becomes fatal.

Currently, clinical testing for CKD is accomplished by calculating a glomerular filtration rate (GFR), which accounts for creatinine levels in a patient. Creatinine levels in a patient are partly a function of the total muscle mass of the patient. However, the equation for calculating GFR may or may not even account for the lean mass of the patient, and even if it does account for the lean mass of the patient, the estimate of lean mass is often inaccurate and is not equivalent to total muscle mass. Total muscle mass is the mass of all the muscle in a human body (which produces the creatinine in the body) while lean mass is the mass of all the organs, skin, bones, body water, and muscles in a human body. Inaccurate measurement of GFR can lead to misdiagnosis of kidney failure (e.g., false positive) or misdiagnosis of a healthy kidney (e.g., false negative) in patients that have above average or below average muscle mass. With a more accurate measurement of GFR, patients can be more accurately diagnosed with fewer tests having to be run on the patients.

BRIEF SUMMARY

Techniques and systems for measurement of muscle mass and calculation of GFR are described. As described herein, the muscle mass measurement can be estimated from medical images such as computed tomography (CT) or magnetic resonance imaging (MRI) images.

A system can be provided that receives an image file of a patient, performs a thresholding process to the image file to generate a contrasted image, and segments pixels of the contrasted image into bone and not bone. The system can distinguish muscle from organ for the pixels segmented as not bone by determining a location of a rib cage of the patient using the pixels segmented as bone and removing pixels segmented as not bone that are located within the rib cage. The system can calculate a volume of muscle based on remaining pixels segmented as not bone; calculate a total muscle mass based on the volume of muscle; and provide the total muscle mass of the patient. The system can further receive a measurement of creatinine levels of the patient, calculate a glomerular filtration rate of the patient based on at least the total muscle mass of the patient and the measurement of creatinine levels of the patient; and provide the glomerular filtration rate.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 1 illustrates a conceptual diagram for calculating GFR, one example application of the described automated determination of muscle mass.

FIG. 2 illustrates an example process flow for automated determination of muscle mass.

DETAILED DESCRIPTION

Figure 3:
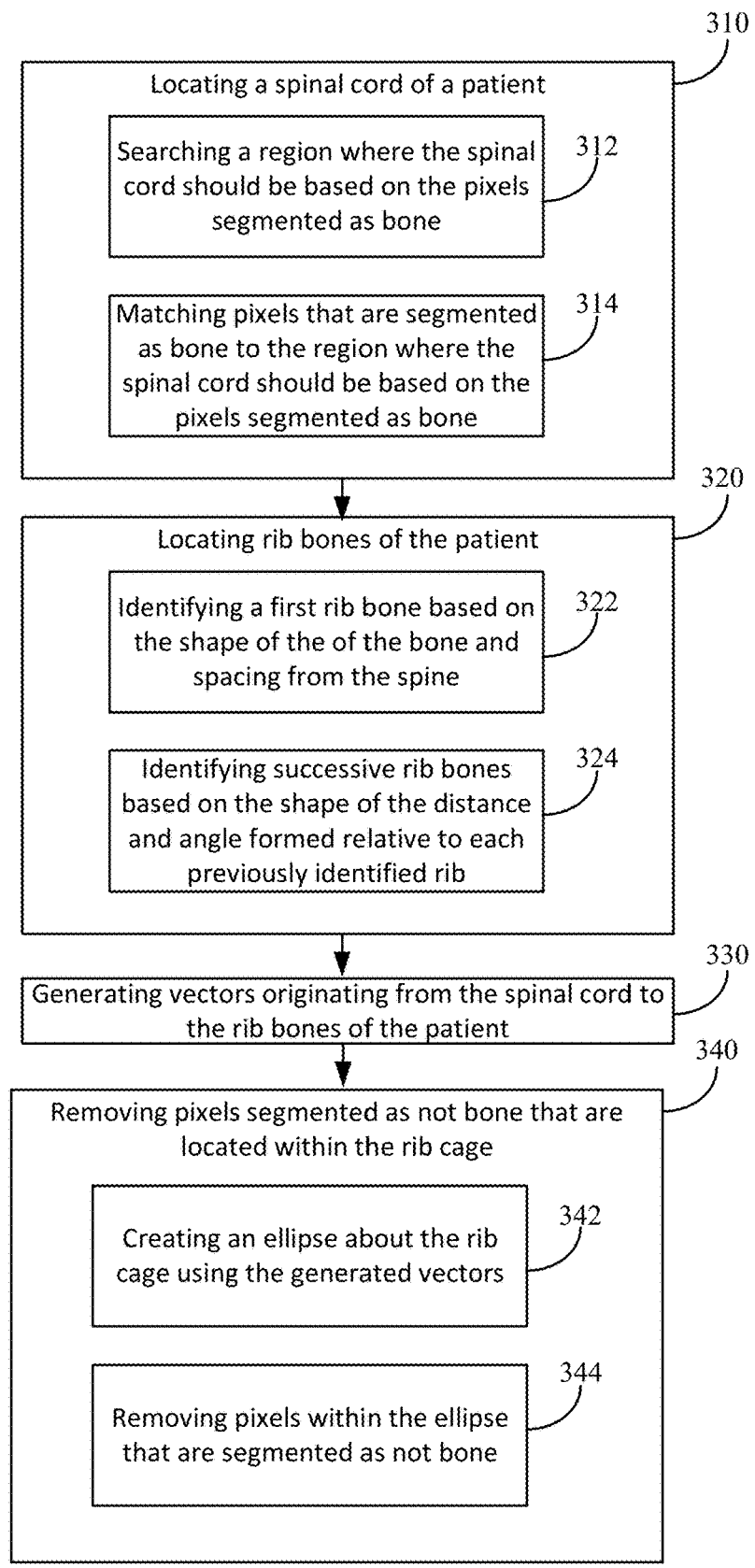
FIG. 3 illustrates an example process flow for determining the location of the rib cage of the patient and removing tissue that is not bone.

Techniques and systems for measurement of muscle mass and calculation of GFR are described. The described techniques utilize medical images to obtain a personalized assessment of muscle mass. An accurate determination of muscle mass is a valuable tool for numerous applications, including assessing a patient's GFR. GFR is used to assess how well a patient's kidneys are functioning, which can help diagnose CKD in a patient. A patient's calculated muscle mass can be used along with other factors, including, but not limited to, creatinine measurements, to calculate GFR. The described system and techniques can stratify the degree of renal kidney dysfunction and thus be used to stratify patients into categories of degrees of renal dysfunction. By enabling the stratification of patients, it is also possible to more efficiently and safely administer appropriate quantities of pharmacological agents (e.g., drugs, medications). In addition, the stratification into categories of degrees of renal dysfunction can then be used for medical research, including but not limited to population and cohort studies, and clinical trials.

In some implementations, the described techniques can produce accurate early detection of CKD. Diagnosing and identifying patients with early CKD can lead to health measures taken to slow the progression of the disease, thereby delaying or preventing the eventual need for dialysis.

Currently in clinical practice, the degree of a patient's renal function is estimated by calculating glomerular filtration rate (GFR), which is a quantitative parameter of how well the patient's kidneys eliminate substances from the body. In current clinical practice, by far the most common method for calculating GFR is by measuring a substance called creatinine in the blood (serum). Creatinine is constantly produced as a byproduct by muscle tissue. Creatinine is eliminated from the body and dumped into the urine by the kidneys. Higher levels of serum creatinine indicate that renal function is decreased, relatively speaking. However, a patient with a larger total body muscle mass produces a greater amount of creatinine than a patient with a lower total body muscle mass. Therefore, if two patients had the same degree of renal function, the patient with greater total body muscle mass would have a higher level of serum creatinine than the patient with the lower total body muscle mass. Thus, being able to accurately determine the total muscle mass of a patient would result in greater accuracy in calculating GFR, and thereby more accurately and precisely determine renal function.

The most commonly used formulas for calculating GFR all use serum creatinine as one of the variables in a formula, but often inaccurate proxy parameters in lieu of total muscle mass, including age, sex, and race. The most commonly used method is the MDRD formula, which does not use body weight at all. Another commonly used method for calculating GFR, the Cockcroft-Gault formula, uses body weight. These formulas may not include total muscle mass because there are no widely used methods for calculating that parameter. For example, hydrostatic underwater weighing is impractical for the vast majority of patients, and electrical impedance measurement provides a crude and relatively inaccurate estimate. Thus, there is a need for a more accurate method for measuring total body muscle mass as a means for more accurately quantifying renal function/dysfunction.

A software program is provided that analyzes a full body CT or MRI scan of a patient, and outputs a total muscle mass and calculated GFR. The described software program can include process 200 such as described with respect to FIG. 2.

FIG. 1 illustrates a conceptual diagram for calculating GFR, one example application of the described automated determination of muscle mass. Referring to FIG. 1, an image from one of the suitable imaging modalities can be received (110) by a system performing the described automated determination of muscle mass, and a muscle mass computation (120) can be performed on the image(s). The suitable imaging modalities can include, but are not limited to, computed tomography (CT) and magnetic resonance imaging (MRI). In the examples presented herein, automated determination of muscle mass is carried out on CT images. However, it should be understood that a similar process can be carried out on other images. Once the muscle mass is computed, the muscle mass value computed from the image(s) can then be used to calculate (130) GFR for the patient.

FIG. 2 illustrates an example process flow for automated determination of muscle mass. Referring to FIG. 2, process 200 includes receiving (202) an image file of a patient. The image file includes data of a 3D image, for example from a full body CT or MRI scan of a patient. Process 200 can further include performing (204) a thresholding process to the image file to generate a contrasted image. In some cases, performing the thresholding process to the image file to generate the contrasted image includes creating a histogram of intensity values for a plurality of image slices found within the image file; calculating maximum and minimum pixel intensity values relative to a threshold value for each of the plurality of image slices; and adjusting each of the plurality of image slices to a gray scale based on the maximum and minimum pixel intensity values for the plurality of image slices.

Once the contrasted image is generated, the process 200 can include segmenting (206) pixels of the contrasted image into bone and not bone. For example, pixels with intensity values indicative of bone can be identified (and labeled) as bone and the remaining pixels can be labeled as not bone. Then, process 200 can include distinguishing (208) muscle from organ for the pixels labeled as not bone. The labeling may be explicit or implicit (e.g., may be a parameter assigned to each pixel or may simply be tracked using a list or other data structure).

Once the pixels identified as being muscle are distinguished from the pixels identified as being organ—and the pixels identified as being organ are removed from the pixels labeled as not bone (e.g., by removing from list or changing the labeling), process 200 can further include calculating (214) a volume of muscle based on the remaining pixels from the group of pixels segmented (and labeled) as not bone; calculating (216) a total muscle mass based on the volume of muscle; and providing (218) the total muscle mass of the patient. In some cases, the distinguishing (208) of the muscle from organ is performed by: determining (210) a location of a rib cage of the patient using the pixels segmented as bone; and removing (212) pixels segmented as not bone that are located within the location of the rib cage.

FIG. 3 illustrates an example process flow for determining the location of the rib cage of the patient and removing pixels corresponding to tissue that is not bone. In this example, determining the location of the rib cage of the patient includes locating (310) a spinal cord of the patient. Locating (310) a spinal cord of the patient can be performed, for example, by: searching (312) a region where the spinal cord should be based on the pixels segmented as bone; and matching (314) pixels that are segmented as bone to the region where the spinal cord should be (e.g., expected to be) based on bone features. Determining the location of the rib cage of the patient can further include locating (320) rib bones of the patient. For example, locating (320) the rib bones of the patient can be performed by: identifying (322) a first rib bone based on shape of the bone and spacing from the spine; and identifying (324) successive rib bones based on the distance and angle formed relative to each previously identified rib. In some cases, determining the location of the rib cage of the patient can further include generating (330) vectors originating from the spinal cord to rib bones of the patient within the 3D image.

Removing (340) pixels segmented as not bone that are located within the location of the rib cage can include creating (342) an ellipse about the rib cage using the generated vectors and removing (344) pixels within the ellipse that are segmented as not bone.

As explained above, GFR can be more accurately calculated with the inclusion of a patient's total muscle mass. The described program (that performs one or more operations of process 200) achieves the inclusion of a patient's total muscle mass in the GFR calculation by calculating the area occupied by muscle in each slice (or digital imaging and communications in medicine (DICOM) file) taken by the MRI or CT machine. DICOM is a standard for handling, storing, printing, and transmitting information in medical imaging.

Pixel intensity and location of pixels are used in order to segment muscle from bone and fat tissue (e.g., during operation 206). However, some tissue types also fall within the predefined range of pixel intensity values as other tissue types. In other words, some tissue types' predefined range of pixel intensity values overlap with each other (e.g., muscles and organs). Accordingly, the described program includes a method of differentiating between tissue types that have an overlapping predefined range of pixel intensity values. According to an implementation, the method of differentiating between tissue types includes searching within the image(s) for regions of the body that are known to include undesirable tissue types for easily identifiable markers. Once the markers are located, the undesirable tissue types are eliminated based on their relative location to the easily identifiable marker. In some embodiments, bones are used because they are easily identifiable in suitable imaging modalities. For example, as indicated by operations 210 and 212 (and described above with respect to FIG. 3), ribs can be located as markers, and organs can be identified from their relative positioning with respect to the ribs in order to support the exclusion of pixels corresponding to organs when identifying regions corresponding to muscle. In some cases, the patient's height (and expected body parts at relative positions with respect to the patient's height) is also used to help eliminate certain regions of the body that are known not to contain the desired tissue type. For example, sections of the image (the 3D image of the full body scan) at the top of the height can have the pixels corresponding to brain inside of the skull eliminated from calculations involving muscle.

Accordingly, after eliminating pixels in regions where the markers and/or height of the patient were used to identify nearby pixels to exclude, the volume of muscle can be calculated from the remaining pixels' area and position of those pixels with respect to the patient's height (e.g., thickness of the slice to which an area is calculated).

The example process for automated determination of muscle mass can further include calculating a volume of bone using the segmented pixels of the contrasted image identified as bone; calculating total bone mass of the patient using the volume of bone; and providing the total bone mass of the patient.

In a specific implementation, the full body scan results in a plurality of slices that are stacked together to create a 3D image of the patient. The area of the pixels that correspond to muscle in a slice is calculated (e.g., the area covered by remaining pixels from operation 208); and data for muscle area of each slice, distance between each slice, and numerical trapezoidal integration (e.g., a trapezoidal integration method) are used to calculate volume of muscle (e.g., for operation 214).

The mass of the desired tissue can then be calculated (e.g., operation 216 for desired tissue of muscle) by multiplying the determined volume of the desired tissue type by the average density for that tissue type. For example, if the desired tissue type is muscle, muscle mass is calculated by multiplying the volume of muscle by average muscle density (e.g., muscle mass=muscle volume*1.06e-6 kg/mm^3). In some implementations, the mass of the desired tissue (e.g., provided in operation 218) is then displayed in a graphical user interface.

Using the patient's total muscle mass, GFR can then be calculated. In addition to calculating a patient's total muscle mass, the software program also has the option of calculating the patient's bone mass and fat tissue mass. The results of the calculations, as well as intermediate steps, can be provided in, for example, a graphical user interface.

The example process for automated determination of muscle mass can further include receiving a measurement of creatinine levels of the patient; and calculating a glomerular filtration rate (GFR) of the patient based on the total muscle mass of the patient and the measurement of creatinine levels of the patient. Calculating the glomerular filtration rate of the patient can also be based on the patient's weight, age, race, and gender.

In some cases, searching a region where the spinal cord should be is further based on a patient's height. In addition, in some cases, matching pixels that are segmented as bone to the region where the spinal cord should be is further based on the patient's height.

In some cases, matching pixels that are segmented as bone to the region where the spinal cord should be based on bone features comprises using location, size, and dimensions of pixels segmented as bone in relation to 1) an overall image size and 2) predefined ranges of bone locations, sizes, and angles.

Figure 4:
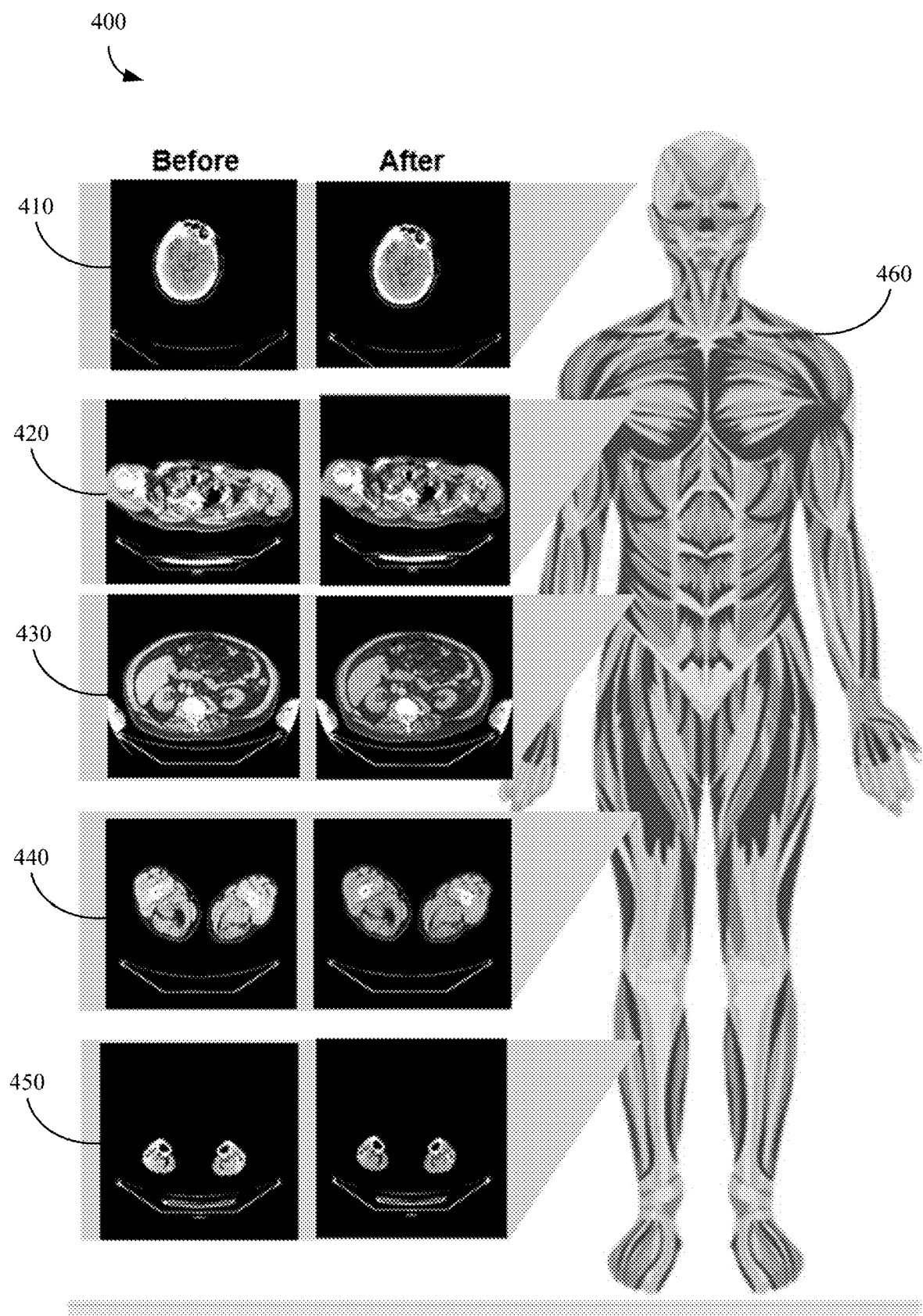
FIG. 4 shows an intermediate stage in an automated determination of muscle mass using computed tomography image slices.

FIG. 4 shows an intermediate stage in an automated determination of muscle mass using computed tomography image slices. In the specific implementation illustrated in FIG. 4, muscle mass is a desired tissue to be found using CT imaging. CT images are produced by using a combination of computer-processed x-ray measurements taken at different angles to produce cross-sectional images. These images (410, 420, 430, 440, 450) can be stacked to create a 3D image representing the patient 460, as well as produce data that can be manipulated to determine various body tissues (muscle, fat, bone, etc.). The image slices are determined to be from a certain region of the body based on the patient's large bone structures contained within the images. Next, the images are contrasted to help distinguish between different types of tissues. For instance, image 410 illustrates the skull and brain tissue contained within the skull. Because of the shape of the bones identified after contrasting the image slice 410, the computer implemented process identifies this image slice 410 as being skull and brain tissue, which can be removed from consideration when calculating muscle mass. Advantageously, contrasting helps identify the boundaries of the bone structures more clearly than the "before" image.

Image 420 illustrates the shoulder and chest region of the body. Because of the shape of the bones identified after contrasting the image slice 420, the computer implemented process identifies this image slice 420 as being in the upper abdomen region of the body, which may include the tissues such as the aorta, heart, liver, kidney, and spinal tissue. These organs may be confused with muscle tissue due to overlapping pixel intensity value ranges with muscle. Therefore, it is advantageous to remove these tissues from consideration when calculating muscle mass. Similarly, image 430 illustrates the abdomen, which may contain liver, kidney, spinal tissue, intestines, and bladder tissue that has overlapping pixel intensity value ranges with muscle. These tissues should also be removed from consideration when determining muscle mass and the program can automatically do so, for example, using the process shown in FIG. 3 or FIG. 5B.

Images 440 and 450 are similarly shown as a before contrasting image and an after contrasting image. The contrasting makes clear the distinction between bone and other tissues. Again, the shape of the images and the bones within the images 440, 450 are used to help identify which part of the body the image slice comes from. As can be seen, these images 440, 450 come from the legs of the patient and are therefore included when computing muscle.

Figure 5A:
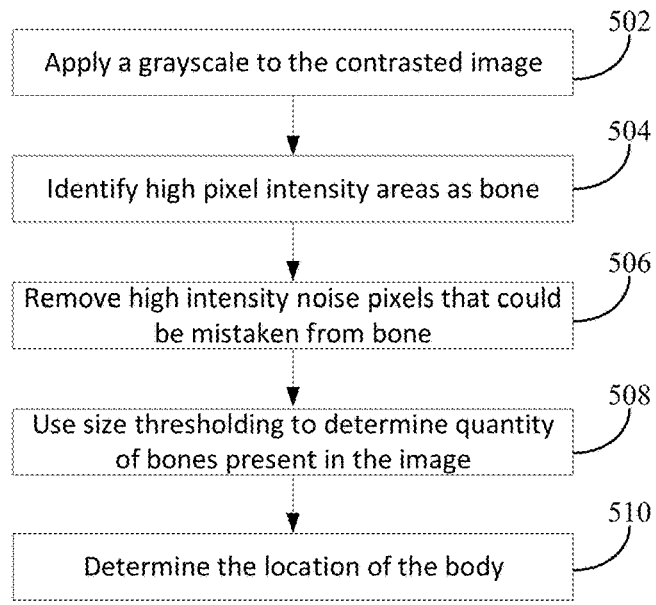
FIG. 5A illustrates an example process for segmenting bone from other tissue types.

FIG. 5A illustrates an example process for segmenting bone from other tissue types. Pixels in the contrasted image are segmented based on matching pixel intensity values and predefined pixel intensity value ranges for tissue types. As illustrated in FIG. 5A, bone is segmented from other tissue types. The computer implemented method begins by analyzing the contrasted image. In a specific implementation, a grayscale is applied (502) to the contrasted image. High pixel intensity regions are identified (504) as bone. Once these regions are identified, image eroding and dilating is applied to the image to remove (506) small noise pixels that could be mistaken as bone (individual high intensity value pixels that are in areas of no other high intensity value pixels). The size of the bones in the image are then examined using size thresholding to determine (508) the quantity of large bone features that exist. Using the number and size of the bones present in the image, the location within the body being analyzed can be determined (510). It should be understood that each tissue type (e.g., muscle) can be segmented in a process similar to the process described in FIG. 7.

Figure 5B:
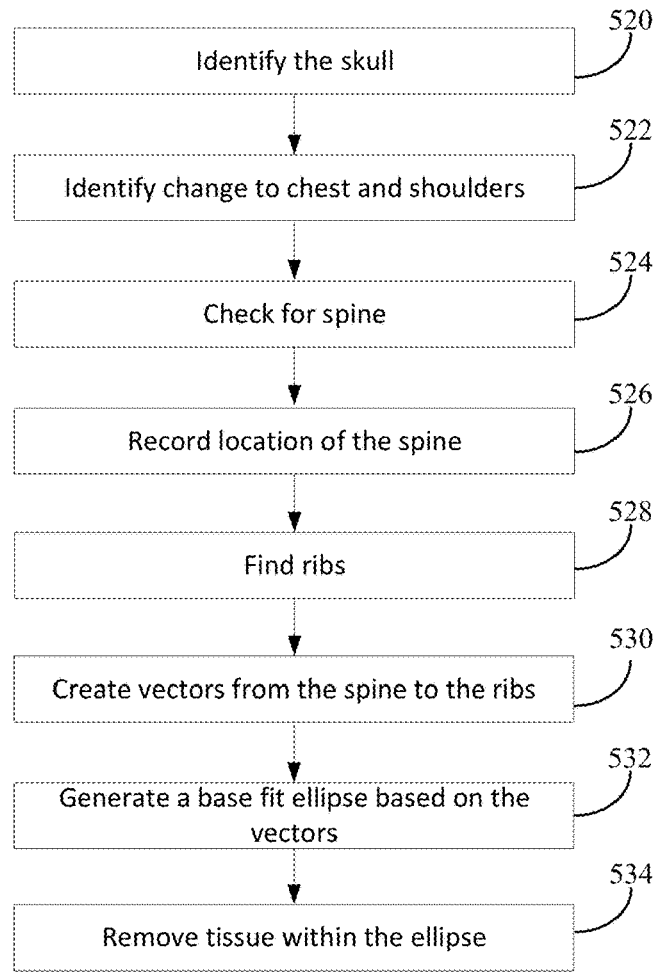
FIG. 5B illustrates an example process for distinguishing muscle from other tissue types.

FIG. 5B illustrates an example process for distinguishing muscle from other tissue types. The computer implemented method also uses the pixels segmented as bone to search within regions of the body for easily identifiable markers. Once the markers are located, organs and other similarly shaded pixels that are not be muscle are eliminated based on their relative location to the easily identifiable marker.

In a specific implementation, the easily identifiable marker is the spine and rib cage of the patient. The spine and/or ribs are found by using the skeleton of the patient, using skull as a reference point and working downwards. The skull is identified (520) as a single large bone structure. As the computer implemented method works downwards, when the bone structures become further spaced out, with relatively large width and height spacing, the change is identified as progressing to the shoulders and chest region (522). Once the chest is identified, the computer implemented method uses the centroid features of all of the discovered large bone structures and checks for the spine (524). The location, size, and dimensions of new large bone structures in relation to the overall image size and predefined ranges of bone locations, sizes, and angles can be analyzed to determine if the spine is present. If the spine is present, the location is recorded (526).

When the spine is identified, a search for ribs takes place (528), and elements considered to be ribs are analyzed to find the outline of the chest cavity. The first rib is discovered by searching the right side of the spine and searching for the closest identified shape of a rib. Once the first rib is discovered, the next rib candidates are weighted based on their distance from the current rib and the angle that is formed from the current rib to the next bone discovered. An optimal rank includes a relatively small distance and relatively small counter-clockwise angle. If the rank is satisfactory, the rib is selected. This process can be iterated over the number of bone structures that are found to the right of the spine. In addition, the same process can be carried out over the left side of the spine, except with the closest bone structure to the left of the spine and the ranking includes a relatively small clockwise angle. Once both halves of the chest cavity are analyzed, if one half has more ribs than the other, the side with more ribs may be used for rib reconstruction through symmetry. Vectors can then be generated from the spine to any located rib bones that are at the same height as the spine to outline the chest cavity.

In this specific implementation, vectors are created (530) from the spine to the ribs. Using these vectors, a "best fit" ellipse is generated (532) that outlines the shape of the ribs/vectors around the spine in order to create a similar shape to the chest cavity. Equations of an ellipse are used to calculate a major axis dimension, a minor axis, and an ellipse center point and angle. A new ellipse is generated for each slice. Once formed, all of the tissue within the ellipse can be removed (534) from consideration as muscle. However, because psoas muscle is just behind the spine and within the elliptical shape of the chest cavity, an angle deviation is used to remove this region from the ellipse. An arc-triangle shape is cut out of the ellipse to allow for the psoas muscles to be considered in the muscle calculations. In addition, pixels with pixel intensity values that do not fall within the range of the desired tissue type are also eliminated, leaving muscle.

Figure 6:
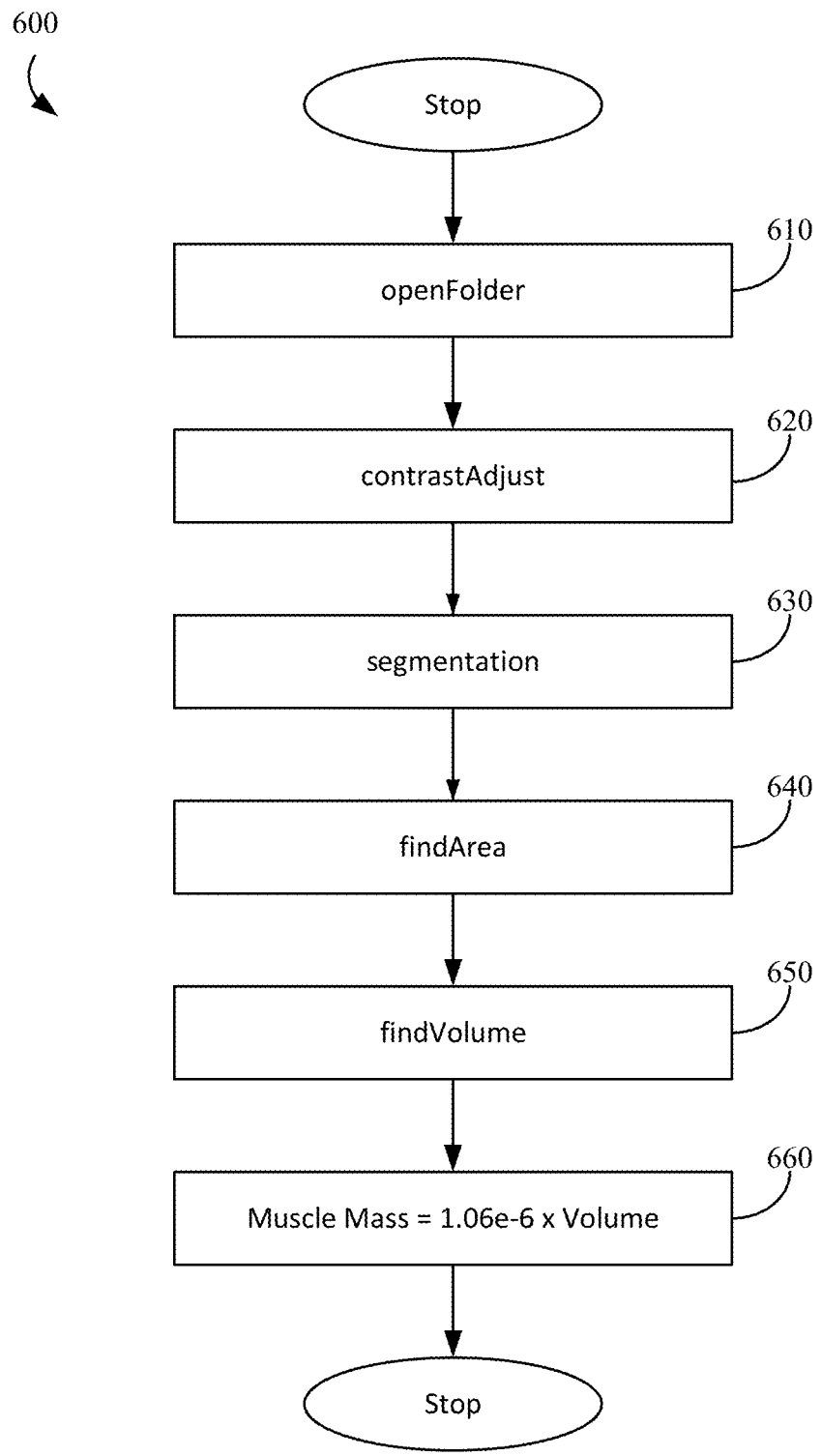
FIG. 6 illustrates a process for calculating muscle mass according to an example implementation.

FIG. 6 illustrates a process for calculating muscle mass according to an example implementation. Referring to FIG. 6, process 600 includes five program modules: openFolder 610, contrastAdjust 620, segmentation 630, findArea 640, and findVolume 650. The output of findVolume 650 is used to calculate the muscle mass 660.

In the example implementation, openFolder 610 displays file selection menu to allow user to select the folder of a medicine (DICOM) file they wish to use. Using vector of file names, the openFolder module finds the files within the specified folder, removes directory files, and necessary header information. This includes each respective image as well as collecting header information from a first DICOM file to obtain the number of files in folder, slice thickness, and pixel dimensions.

In a specific example, the openFolder function opens the file explorer so the user may select the folder containing DICOM images for analysis. Once the folder is selected, the header of the DICOM file is read in order to obtain information regarding the number of slices from the CT scan, the thickness of each slice, the pixel spacing of the images, and the images from the CT scan themselves. This data (number of slices, thickness of each slice, pixel spacing of the images, and the images themselves) is stored and used by the program to perform the automated determination of muscle mass.

ContrastAdjust 620 takes an un-contrasted DICOM image and creates a histogram of its pixel intensity values.

Figure 7:
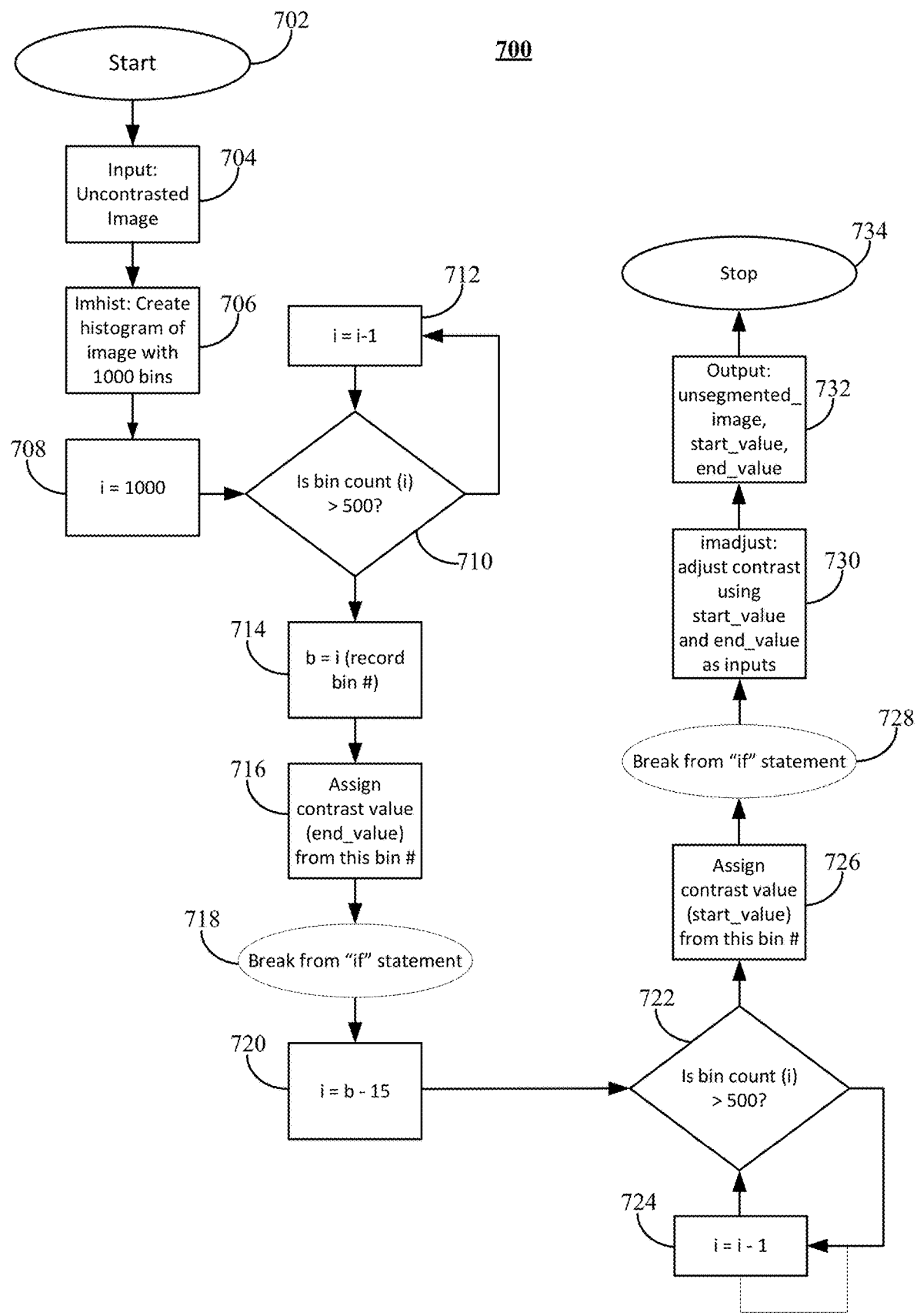
FIG. 7 illustrates an example contrast process for automated determination of muscle mass.

FIG. 7 illustrates an example contrast process 700 for automated determination of muscle mass. A contrast image function starts (702) either by the direction of a user or automatically when an uncontrasted image is received (704) by the function. This process then iterates through the bins by starting at the lower limit of intensity values and increasing until a threshold of the bin count is reached, and then records this location. Specifically, referencing this implementation, 1000 bins are created (706). Beginning with i (bin count)=1000 (bins) (708), the bin count is checked to see if i>500 (710). If i is not greater than 500, the function moves to the next bin (712). If i>500, the b (bin number) is recorded (714). Contrast values are then assigned based on bin number (716). The process then implements a break from the "if" statement (718), moves 15 bins to the left (720), and iterates through the bins again, this time starting at the upper limit for intensity values and decreasing until a threshold of the bin count is reached, and then records this location. Specifically, the bin count is checked to see if i<500 (722). If i is not less than 500, the function moves to the next bin (724). If i<500, contrast values are assigned based on this bin location (726). The process then implements a break from the "if" statement (728). Finally using the two found bin locations, the image is contrasted to have the maximum and minimum pixel intensity values (730). The function 700 returns a newly contrasted image (732) and the function is stopped (734). It should be understood that the number of bins and bin counts are a matter of design choice and the number is not intended to be limiting.

As in the specific example shown in FIG. 7, subcomponent module of contrastAdjust 620 iterates through the histogram looking for when a threshold of intensity values is reached for a maximum relative intensity and a minimum. The image is contrasted based on the maximum and minimum values discovered.

Although the DICOM images are obtained with a windowing and span that is optimal for tissue differentiation, further contrasting is done in order to create a greater contrast in the pixel intensities of the tissue types. To perform this, the "uncontrasted" image that was within the DICOM file is passed into the function. The function creates a histogram of intensity values found within the image. Once the histogram is created, the process iterates through the bins starting at the lowest intensity value until it reaches a threshold of the bin count and notes this location. It then does the same thing starting at the upper limit of intensity values and decreasing. Once the two locations are discovered, the image is set to a contrast that has a minimum and maximum intensity of the values found, and outputs this new image.

It should be noted that contrasting to find tissue types is useful for classifying bones from other tissue types, classifying muscle and organs from other tissue types, and fat from air inside the body. Furthermore, fat and air can be differentiated by adjusting a contrasting threshold.

Segmentation 630 can include numerous processes including IsolateBones. IsolateBones includes the processes described in FIGS. 5A and 5B. IsolateBones is carried out on the contrasted image. In general, the centroid location is identified and the area of each bone structure, from which the location of the slice in the body is determined. If an image slice is determined to include a chest area, internal organs are removed. The first call of this function (first slice of the scan) will identify and remove the scanner, and remove the scanner from all subsequent slices, while also excluding initial slices from consideration while large regions of the scanner are still present and specific bone structures cannot be identified.

In particular, with reference again to FIGS. 5A and 5B, IsolateBones starts by analyzing the newly contrasted image. The program begins by setting (502) the image to a grayscale and examining (504, 520) high intensity regions, bone. Once these areas are identified, image eroding and dilating is used in order to remove (506) small noise pixels within the image. This does not affect any part of the image except individual high intensity pixels that are in areas of no other high intensity values. The function then examines the size of the bones in the image using (508) size thresholding to determine the quantity of large features that exist. Using the number and size of bone structures preset, the location of the slice relative to the body can be determined. This is found in the function LocateSlice. The number of isolated bone features, previous slice location, large bone features, and image matrix size is passed into the function. The function uses this information to output the relative location of the slice in the body, if any ribs were present in the slice and their coordinates if present, as well as the spine position. If ribs are present and the slice is within the chest cavity, the rib positions, image and spine position are passed into RemoveInsides so that the tissue inside the chest cavity can be removed from muscle consideration. During this time the function also identifies the CT scanner in the first image and "removes" the scanner from all sequential images by eliminating its pixels from muscle consideration.

LocateSlice classifies (510) the region of the body a slice is located in based on number of large bone features and sequential information. This function tracks the location of the spine (while present) for spatial consideration in removing desired tissue from consideration as muscle (i.e. organs). See CheckForSpine for special consideration based on bone location and FindRibs for removing internal organs. This function is within the IsolateBones function and is used to examine what part of the body the slice is from by identifying if the spine is present and or any ribs. The number of isolated bone features found in IsolateBones, previous slice location, large bone features, and image matrix size is passed into the function. The function begins by checking (524) is a spine is present within the slice. This is done by using (520) the skull as a reference point and searching for a single large bone structure within. As the slices progress, if the bone structures become further spaced out, with a relatively large width and height spacing, the program identifies (522) this change as progressing to the shoulders and chest region. Once in the chest, as identified by the program, CheckForSpine is called to ensure the correct positioning of the spine coordinates. The spine position (averaged from previous iterations, or empty at first call), centroid locations of all large bone features are passed into the function and if the spine is present and the spine's pixel locations are outputted back to LocateSlice. Once identified, the ribs are found and analyzed to be able to find the outline of the chest cavity. This is done in the function FindRibs. The function is inputted with the discovered bone features of the slice and the spine position for reference. From this the location of the ribs are placed into a vector with x coordinates, y coordinates, and angle.

CheckForSpine uses all previous spine locations with a moving average to identify (524) the approximate region that the spine should be located and identifies the nearest bone feature (within a range) as the spine location for the current slice. This function is called within the LocateSlice function. The function is inputted with the last spine position, zero if the first slice, and the centroid features of all the discovered large bone structures. The function then analyses the location of the new large bone structures in relation to averaged spine location to determine if the spine is present and if so, updates (526) the location and outputs the location back to LocateSlice.

FindRibs (528) creates (530) vectors where the spinal cord is the origin, and iterates through possible rib candidates to determine the shape of the chest cavity through distance and angle from the spine. It starts by looking to the right of the spine and weighting candidates in terms of distance and angle. Once the first rib is discovered it moves counter-clockwise to identify adjacent ribs.

This function is called within the LocateSlice function. This function is called upon when the slice is deemed to be within the chest. It is used to find the location of ribs present within the slice and efficiently sort them to be able to distinguish them individually surrounding the spine. This function receives the spine position and the centroid features of bones discovered within the slice. The first rib is discovered by evaluating the right side of the spine and searching for the closest identified "rib". If no rib is present then the function is terminated and no ribs are identified. Once the first rib is discovered, the next rib candidates are weighted based on their distance from the current rib and the angle that is formed from the current rib to the one being examined. If the rank is most optimal (e.g., a small distance and a small counter-clockwise angle), then the rib is selected. This is iterated over the number of ribs that were discovered. It should be understood that although the described implementation starts with the rib on the right, analysis may be carried out simultaneously with the left or even start first with the left rib, depending on the implementation.

The ribs are analyzed until the x-coordinate is the same as the spine position. This indicates that the function started just to the right of the spine and moved in a counter-clockwise direction until it was directly above the spine, at some arbitrary height. The same ranking and iteration was done for the left side of the spine by evaluating the closet rib to the left and moving in a clockwise direction until the software was at the x-coordinate of the spine. Once the two halves of the chest were analyzed, if one side of the chest had less ribs discovered then the other side, the side with more ribs could be used for rib reconstruction through symmetry. By evaluating each side independently and then evaluating the two sides, a better reconstruction can be created. If the two halves had a relatively similar amount of ribs located, then no symmetry needs to be applied and the rib positions can be analyzed as found. The chest reconstruction is done with the ellipse_fit function within RemoveInsides. RemoveInsides calls ellipse_fit to create an ellipse about the ribs and spine to create a mask for removal (534) of the internal organs from within the chest cavity as consideration for muscle.

Figure 8A:
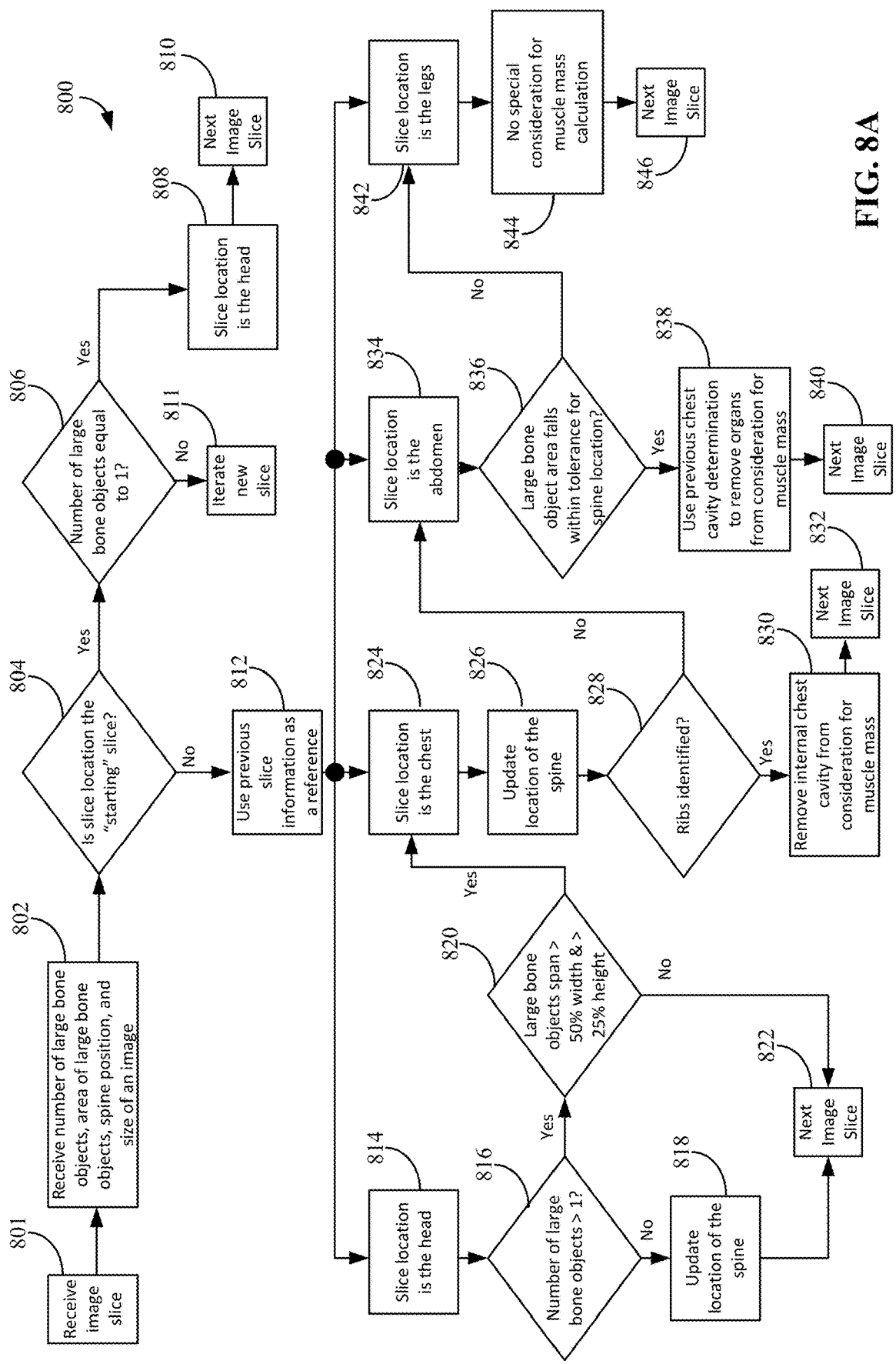
FIG. 8A illustrates a process for identifying image slice location in the body and removing undesirable tissue types according to an example implementation.

FIG. 8A illustrates a process for identifying image slice location in the body and removing undesirable tissue types according to an example implementation. As shown in FIG. 8A, location, size, and dimensions of new large bone structures in relation to the overall image size and predefined ranges of bone locations, sizes, and angles can be analyzed to determine if the spine is present. For this implementation, the computer implemented process iterates through the image slices beginning with the image slice for the top of the patient's head to the image slice of the bottom of the patient's feet. In some cases, this process may be implemented beginning with the bottom of the patient's feet up to the top of the patient's head, as well as be implemented for a certain region(s) of the patient's body (e.g., the patient's chest and abdomen).

The computer implemented process receives (801) an image slice along with the (802) large bone objects, area (relative to total number of pixels) of the large bone objects, the spine's position and the overall size of the image being analyzed. Next, the process determines (804) whether the image slice is the first or "starting" image slice. If yes, the process determines (806) whether the number of large bone objects is equal to one. If yes, the image slice location is determined to be the head (808). The process reaches next image slice (810) and begins the iteration over again at step 802. Since this embodiment is designed to begin with the top of the patient's head, if the process determines that the answer to whether the number of large bones is not equal to one, the process reaches iterate new slice (811), the process would iterate through each successive slice until a single bone in an image slice is found.

Turning to a subsequent image slice, the process receives (802) large bone objects, area of the large bone objects, the spine's position and the overall size of the image being analyzed. Next, the process determines (804) whether the image slice is the first or "starting" image slice. If no, the process uses (812) the previous slice information as a reference. Since the previous image slice location was the head (808), the process assumes the slice location is the head (814). Next, the process determines (816) whether the number of large bone objects is greater than one. If no, the process updates (818) the location of the spine and reaches next image slice (822). If yes, the process determines (820) whether the large bone objects span greater than 50% of the width and 25% of the height of the image. If no, the process reaches next image slice (822). If yes, the process assumes the slice location is the chest (824) and continues through the iteration path.

Turning to one of the next subsequent image slices, assuming the slice location is the chest (824), the process updates (826) the location of the spine. Next, the process determines (828) whether any ribs are identified. If yes, the process removes the internal chest cavity from consideration for muscle mass (830) and reaches next image slice (832). If no, the process assumes the slice location is the abdomen (834).

Turning to one of the next subsequent image slices, assuming the slice location is the abdomen (834), the process determines (836) whether the large bone object area falls within a tolerance for the spine location. If yes, the process uses (838) the previous chest cavity determination to remove organs from consideration for muscle mass and reaches next image slice (840). If no, the process assumes the slice location is the legs (842).

Turning to one of the next subsequent image slices, assuming the slice location is the legs (842), the process determines (844) from anatomy that no tissue that overlaps with the pixel intensity value range for muscle within the legs, therefore allowing the computer implemented process to calculate volume and mass of the desired tissue type and reach next image slice (846). It should be understood that the number of image slices are a matter of design choice and the number is not intended to be limiting. The processes illustrated in FIG. 8A can be called within the IsolateBones function. This function is used to remove the tissue from within the chest cavity for muscle consideration and calculation.

Figure 8B:
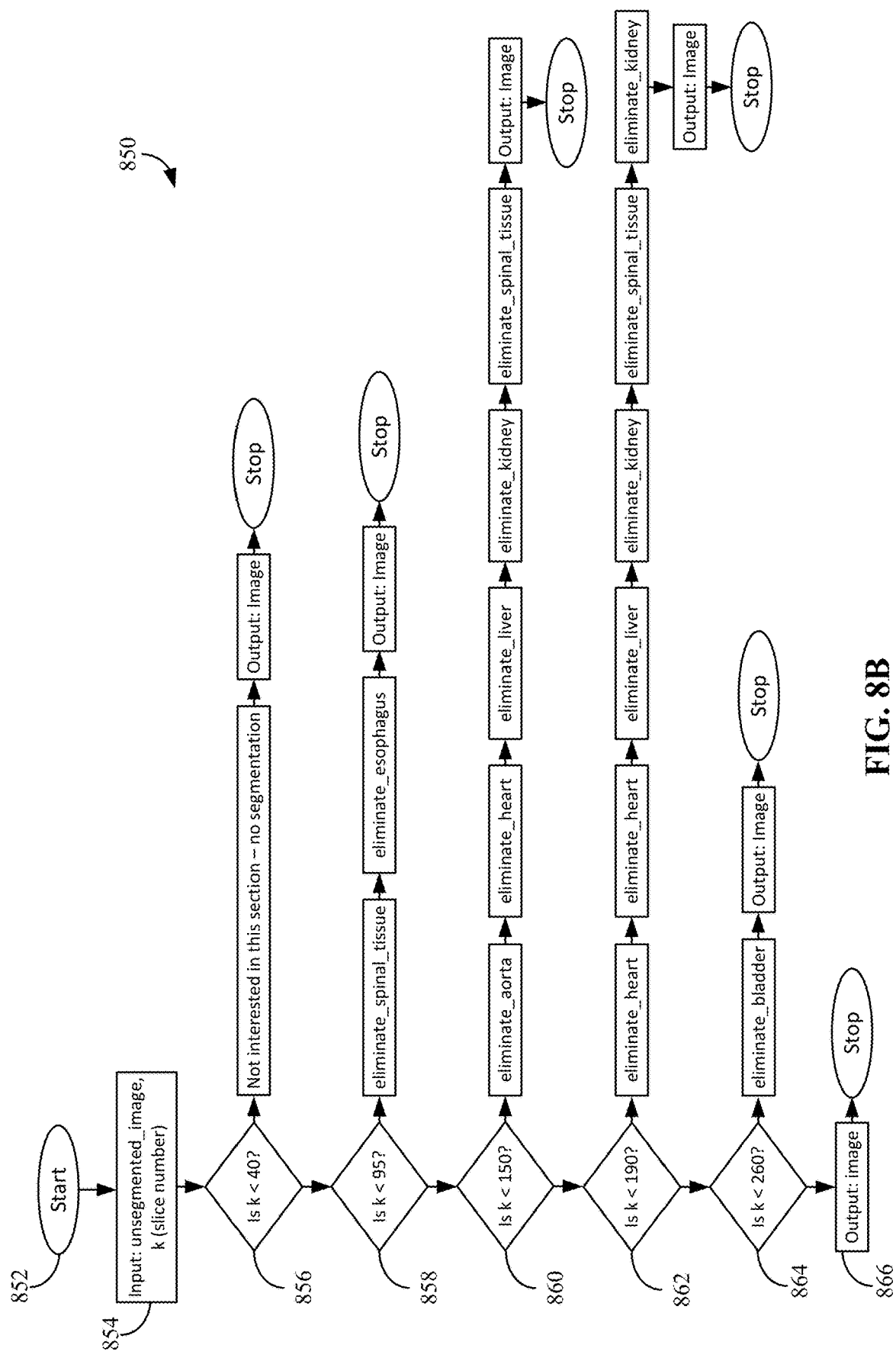
FIG. 8B illustrates a process for identifying image slice location in the body and removing undesirable tissue types according to an example implementation.

FIG. 8B illustrates a process for identifying image slice location in the body and removing undesirable tissue types according to an example implementation. As shown in FIG. 8B, the height of a patient can be used to determine what region to the body should be appearing so that a computer implemented method can search for features that are easily identifiable. Knowing that each sliced image has a certain width and that all of the widths added together equal the patient's height, once the computer implemented method receives the patient's height, a determination for each sliced image can be made as to what body parts the slice may potentially contain based on known anatomy of the human body. In other words, the image slices can be determined to be from a certain region of the body based on the patient's height and the large bone structures contained within the images.

For instance, some regions of the body shown (brain, chest, upper abdomen, middle abdomen, lower abdomen, and legs), may contain certain body tissue types that may need to be removed from the image after segmentation has been performed due to overlapping pixel intensity values with the desired tissue type.

Again, referring to the specific implementation of FIG. 8B, the function can start (852) by numbering (854) each of the sliced images, beginning from the top of the head as one and down to the feet. Specifically, in this embodiment, knowing that the sliced images begin from the top of a patient's head and are numbered down to the feet as well as the patient's height and the width of each sliced image, the computer implemented method determines (856) that the first thirty-nine images will contain brains and skull. Since, in this embodiment, the method is searching for muscle, the first thirty-nine images can be removed from consideration as the muscle mass for the face is negligible for the desired calculation in this implementation. Next, the method checks (858) for the next chest and shoulder areas, knowing that the image slices numbered between forty and ninety-four are likely to fall within this range. As mentioned above, other tissue types also fall within the predefined range of values for muscle, including organs. Because organs fall within the predefined range of values for muscle, they need to be excluded when calculating muscle mass from the contrasted image. This process can be repeated for the upper abdomen (860), middle abdomen (862), and lower abdomen (864), removing the organs that fall within the pixel intensity value range for muscle. Once the legs are reached (866), it is known from anatomy that no tissue that overlaps with the pixel intensity value range for muscle is found within the legs, therefore allowing the computer implemented method to then calculate volume and mass of the desired tissue type. It should be understood that the number of image slices are a matter of design choice and the number is not intended to be limiting. The processes illustrated in FIG. 8B can be called within the IsolateBones function. This function is used to remove the tissue from within the chest cavity for muscle consideration and calculation.

It should be understood that these implementations are described using images taken within the axial plane of the patient's body, however, implementations using other easily identifiable markers may be used to implement the same or similar features as described above using images taken within the coronal or sagittal plane. Furthermore, implementations are contemplated that use a combination of the axial, coronal, and/or sagittal plane of the patient's body to implement the same or similar features as described above.

In a specific implementation, the IsolateBones function receives the x and y coordinates of the identified ribs, the contrasted image with the scanner removed, and the current position of the spine. From this, a function ellipse_fit is used to construct a best fit ellipse that outlines the position of the ribs in order to create a similar shape to the chest cavity. Once this ellipse is formed, all tissue types inside of the ellipse are no longer used for muscle consideration. However, since the psoas muscle is just behind the spine and within the elliptical shape of the chest cavity, and angle deviation is used to include this region when calculating muscle mass. An arc-triangle shape is cut out of the ellipse to allow for the psoas muscles to be considered in the muscle calculations. Once the elliptical shape with the removed section is overlaid with the scanner removed image, a new image is formed and outputted from the function.

Ellipse_fit generates an ellipse about the ribs and spine for use in creating a mask to exclude internal chest cavity from consideration in muscle area calculation. Ellipse_fit can be used as part of the process described in FIG. 5B, for example, as part of generating (532) a best fit ellipse based on the vectors. Ellipse_fit can be carried out within the RemoveInsides function. Ellipse_fit creates an elliptical shape that follows the ribs in order to reproduce the chest cavity shape. The x and y coordinates of the ribs are inputted into the function, and using various equations of an ellipse, a major axis dimension, minor axis, ellipse center point and angle are calculated and outputted. This function creates a new ellipse for each image based on the ribs' locations.

In some cases, the operator can have the option of modifying the program's automatic segmentation before moving forward.

FindArea 640 finds locations of pixels within a contrasted DICOM image that fall into the range of pixel values for muscle. The FindArea 640 function can calculate the total area the pixels occupy in the image. In the example implementation, pixel spacing values are used to convert the pixels to area values.

FindArea 640 can be used to find the area of muscle within each slice. A graphical user interface can use the output of the FindArea 640 function to overlay the muscle pixels with a green color. FindArea 640 receives the contrasted image with the scanner and internal organs removed from IsolateBones, the original contrasted image, and the pixel size from the DICOM header found in openFolder. Each pixel is examined and determined to be muscle or a non-muscle tissue type. This is done by the use of a minimum and maximum threshold intensity value for muscle. If a pixel falls within this specified range, then the pixel is considered muscle and is given a green overlay. Once all of the pixels have been iterated through, the sum of the pixels can be calculated, and an area value is outputted along with the colored image.

FindVolume 650 uses previously calculated areas of each slice (DICOM image), distance between each slice (e.g., slice thickness), and numerical trapezoidal integration to find volume of muscles in body. Furthermore, it should be noted that slice thicknesses for each image may be different. This function is used to calculate a total muscle mass from the area of muscle found in findArea 640. To be able to accomplish this, the function receives the area found in findArea 640, and the slice thickness from openFolder 610. The function uses the slice thickness and a trapezoidal integration method to calculate a volume from each image to result in a total muscle mass which is outputted and displayed in the GUI. It should be noted that any suitable method for calculating volume can be used, including, but not limited to, Simpson's Rule and Reimann sum.

Figure 9:
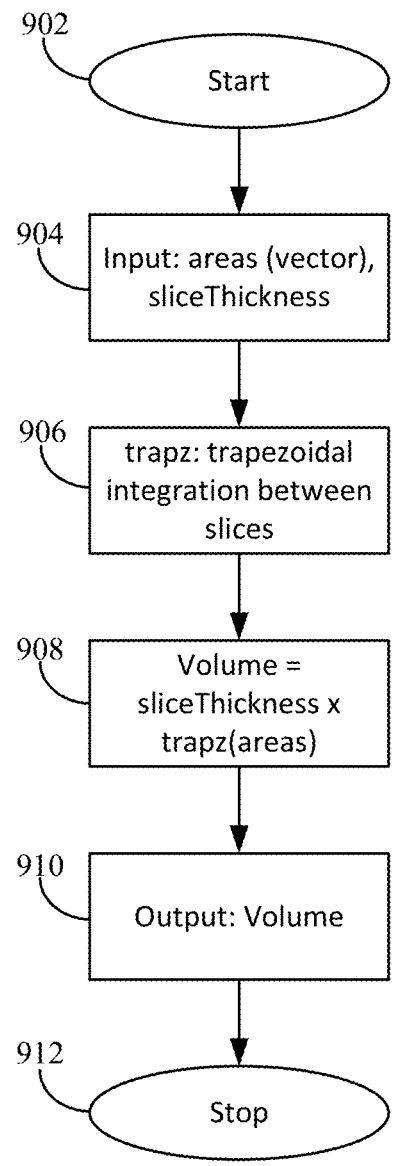
FIG. 9 illustrates a process for calculating a volume of muscle mass according to an example implementation.

FIG. 9 illustrates an embodiment for calculating volume of a tissue type from image slices. The process, which may be carried out as findVolume 650, starts (902) by receiving (904) the overall area of desired pixel intensity value tissue types. A trapezoidal integration method is then applied (906) to determine a best fit trapezoid area in between the image slices. The volume is then calculated (908) by multiplying the slice thickness of each image slice by the determined trapezoid area. The output is then provided (910) to the user and the function stops (912).

Figure 10:
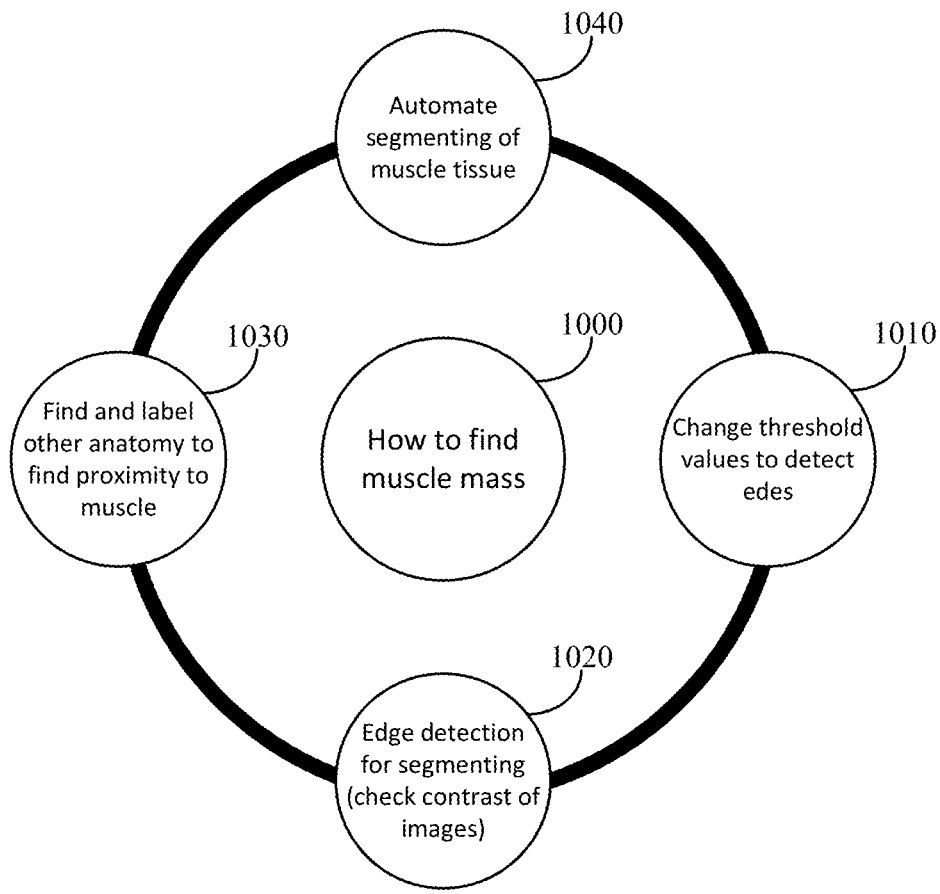
FIG. 10 illustrates an example process for automated segmenting of muscle tissue.

FIG. 10 illustrates a conceptual process 1000 of calculating muscle mass. This process is an implementation that corresponds to the segmentation (630) program module described with respect to FIG. 6. In this conceptual process 1000, threshold values are changed (1010) to detect edges of different types of tissue types. Next, edges are detected (1020) so that the tissue types can be segmented. Other anatomy (e.g., bone structures) are found and labeled (1030) to find relative proximity to muscle. Finally, muscle tissue is segmented (1040) automatically.

Figure 11:
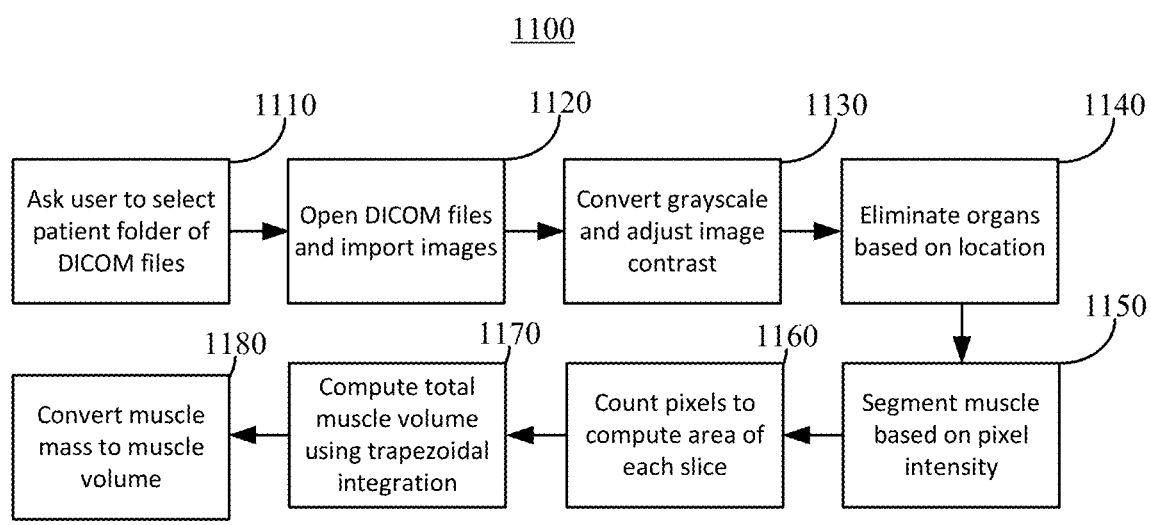
FIG. 11 illustrates an example process for calculating mass from in a patient from a DICOM image.

FIG. 11 illustrates an example process 1100 for calculating mass from in a patient from a digital imaging and communications in a DICOM image/file according to an example implementation, which may be implemented by the process 600. In the example implementation, a user is asked to select (1110) a folder that corresponds to a patient's DICOM files. The DICOM files are opened and the images are imported (1120). This includes each respective image as well as the collection of header information from a first DICOM file to obtain the number of files in the folder, slice thickness, and pixel dimensions.

Next, the process 1100 converts the images to grayscale and adjusts (1130) the image contrast. Based on a patient's height (corresponding to the number of slices) or based on the recognition of bone structures in the images, organs can be eliminated (1140) from the images. This is done so that the organs are not taken into account when calculating the volume of muscle in the patient's body. The remaining body tissue is then segmented (1150) as muscle and not muscle based on pixel intensity. The pixels that are segmented as muscle are counted (1160) to compute the area of each slice. The total volume of muscle in the patient's body is then calculated (1170) using the trapezoidal integration method. Then, to find the total muscle mass needed for the calculation of GFR, the total volume of muscle is converted (1180) to total muscle mass using the formula: muscle mass=muscle volume*$1.06\text{e-}6$ kg/mm$^3$.

Figure 12:
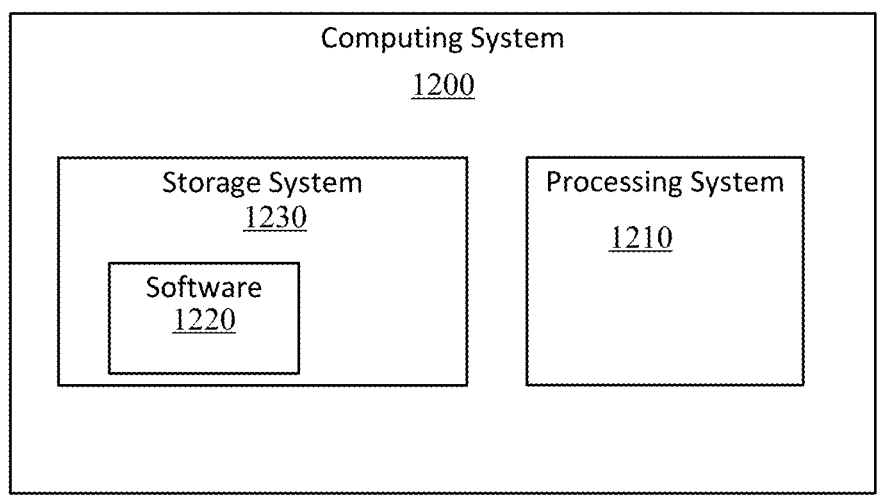
FIG. 12 illustrates an example computing system that may be used in certain embodiments.

FIG. 12 illustrates components of a computing system that may be used in certain embodiments described herein. Referring to FIG. 12, system 1200 may be implemented within a single computing device or distributed across multiple computing devices or sub-systems that cooperate in executing program instructions. The system 1200 can include one or more blade server devices, standalone server devices, personal computers, mobile devices, routers, hubs, switches, bridges, firewall devices, intrusion detection devices, mainframe computers, network-attached storage devices, and other types of computing devices.

Processing system 1210 of computing system 1200 can include one or more processors (e.g., CPU, GPU) and/or other circuitry that retrieves and executes software 1220 from storage system 1230. Processing system 1210 may be implemented within a single processing device but may also be distributed across multiple processing devices or sub-systems that cooperate in executing program instructions.

Storage system(s) 1230 can include any computer readable storage media readable by processing system 1210 and capable of storing software 1220. Storage system 1230 may be implemented as a single storage device but may also be implemented across multiple storage devices or sub-systems co-located or distributed relative to each other. Storage system 1230 may include additional elements, such as a controller, capable of communicating with processing system 1210. Storage system 1230 may also include storage devices and/or sub-systems on which data is stored.

Software 1220, including routines for performing computer implemented processes described above with respect to FIGS. 2-9, may be implemented in program instructions and among other functions may, when executed by system 1200 in general or processing system 1210 in particular, direct the system 1200 or processing system 1210 to operate as described herein. System 1200 may represent any computing system on which software 1220 may be staged and from where software 1220 may be distributed, transported, downloaded, or otherwise provided to yet another computing system for deployment and execution, or yet additional distribution.

Alternatively, or in addition, the functionality, methods and processes described herein can be implemented, at least in part, by one or more hardware modules (or logic components). For example, the hardware modules can include, but are not limited to, application-specific integrated circuit (ASIC) chips, field programmable gate arrays (FPGAs), system-on-a-chip (SoC) systems, complex programmable logic devices (CPLDs) and other programmable logic devices now known or later developed. When the hardware modules are activated, the hardware modules perform the functionality, methods and processes included within the hardware modules.

Embodiments may be implemented as a computer process, a computing system, or as an article of manufacture, such as a computer program product or computer-readable medium. Certain methods and processes described herein can be embodied as software, code and/or data, which may be stored on one or more storage media. Certain embodiments of the invention contemplate the use of a machine in the form of a computer system within which a set of instructions, when executed, can cause the system to perform any one or more of the methodologies discussed above. Certain computer program products may be one or more computer-readable storage media readable by a computer system (and executable by a processing system) and encoding a computer program of instructions for executing a computer process. It should be understood that as used herein, in no case do the terms "storage media", "computer-readable storage media" or "computer-readable storage medium" consist of transitory carrier waves or propagating signals. Instead, "storage" media refers to non-transitory media.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts that would be recognized by one skilled in the art are intended to be within the scope of the claims.

What is claimed is:

1. A computer implemented method comprising:
   receiving an image file of a patient, the image file comprising data of a 3D image;
   performing a thresholding process to the image file to generate a contrasted image;
   segmenting pixels of the contrasted image into bone and not bone;
   distinguishing muscle from organ for the pixels segmented as not bone by:
      determining a location of a rib cage of the patient using the pixels segmented as bone by:
         locating a spinal cord of the patient by:
            searching a region where the spinal cord should be based on the pixels segmented as bone; and
            matching pixels that are segmented as bone to the region where the spinal cord should be based on bone features;
         locating rib bones of the patient by:
            identifying a first rib bone based on shape of the bone and spacing from a spine; and
            identifying successive rib bones based on a distance and angle formed relative to each previously identified rib; and
         generating vectors originating from the spinal cord to rib bones of the patient; and
      removing pixels segmented as not bone that are located within the location of the rib cage;
   calculating a volume of muscle based on remaining pixels segmented as not bone;
   calculating a total muscle mass based on the volume of muscle; and
   providing the total muscle mass of the patient.

2. The method of claim 1, wherein removing pixels segmented as not bone that are located within the location of the rib cage comprises creating an ellipse about the rib cage using the generated vectors and removing pixels within the ellipse that are segmented as not bone.

3. The method of claim 1, wherein searching a region where the spinal cord should be is further based on a patient's height; and
  matching pixels that are segmented as bone to the region where the spinal cord should be is further based on the patient's height.

4. The method of claim 1, wherein matching pixels that are segmented as bone to the region where the spinal cord should be based on bone features comprises using location, size, and dimensions of pixels segmented as bone in relation to:
  an overall image size; and
  predefined ranges of bone locations, sizes, and angles.

5. The method of claim 1, wherein performing the thresholding process to the image file to generate the contrasted image comprises:
  creating a histogram of intensity values for a plurality of image slices found within the image file comprising the 3D image;
  calculating maximum and minimum pixel intensity values relative to a threshold value for each of the plurality of image slices; and
  adjusting each of the plurality of image slices to a gray scale based on the maximum and minimum pixel intensity values for the plurality of image slices.

6. The method of claim 1, further comprising calculating a volume of bone using the segmented pixels of the contrasted image identified as bone.

7. The method of claim 6, further comprising calculating total bone mass of the patient using the volume of bone; and
  providing the total bone mass of the patient.

8. The method of claim 1, further comprising:
  receiving a measurement of creatinine levels of the patient; and
  calculating a glomerular filtration rate of the patient based on the total muscle mass of the patient and the measurement of creatinine levels of the patient.

9. The method of claim 8, wherein calculating the glomerular filtration rate of the patient is further based on a patient's weight, age, race, and gender.

10. One or more computer readable storage media having program instructions stored thereon that, when executed by a processing system, direct a system to:
  perform a thresholding process to an image file of a patient to generate a contrasted image;
  segment pixels of the contrasted image into bone and not bone;
  distinguish muscle from organ for the pixels segmented as not bone by:
    determining a location of a rib cage of the patient using the pixels segmented as bone by:
      locating a spinal cord of the patient by:
        searching a region where the spinal cord should be based on the pixels segmented as bone; and
        matching pixels that are segmented as bone to the region where the spinal cord should be based on bone features;
      locating rib bones of the patient by:
        identifying a first rib bone based on shape of the bone and spacing from a spine; and
        identifying successive rib bones based on a distance and angle formed relative to each previously identified rib; and
      generating vectors originating from the spinal cord to rib bones of the patient; and
    removing pixels segmented as not bone that are located within the location of the rib cage;
  calculate a volume of muscle based on remaining pixels segmented as not bone;
  calculate a total muscle mass based on the volume of muscle; and
  provide the total muscle mass of the patient.

11. The media of claim 10, wherein the instructions to perform the thresholding process to the image file to generate the contrasted image direct the system to:
  create a histogram of intensity values for a plurality of image slices found within the image file comprising a 3D image;
  calculate maximum and minimum pixel intensity values relative to a threshold value for each of the plurality of image slices; and
  adjust each of the plurality of image slices to a gray scale based on the maximum and minimum pixel intensity values for the plurality of image slices.

12. The media of claim 10, further comprising instructions that direct the system to calculate a volume of bone using the segmented pixels of the contrasted image identified as bone.

13. The media of claim 12, further comprising instructions that direct the system to:
  calculate total bone mass of the patient using the volume of bone; and
  providing the total bone mass of the patient.

14. The media of claim 10, further comprising instructions that direct the system to:
  receive a measurement of creatinine levels of the patient; and
  calculate a glomerular filtration rate of the patient based on the total muscle mass of the patient and the measurement of creatinine levels of the patient.

15. The media of claim 14, wherein the instructions to calculate the glomerular filtration rate of the patient is further based on the patient's weight, age, race, and gender.

16. A system comprising:
  a processor directed to:
    receive an image file of a patient, the image file comprising computed tomography images;
    perform a thresholding process to the image file to generate a contrasted image;
    segment pixels of the contrasted image into bone and not bone;
    distinguish muscle from organ for the pixels segmented as not bone by:
      determining a location of a rib cage of the patient using the pixels segmented as bone by:
        locating a spinal cord of the patient by:
          searching a region where the spinal cord should be based on the pixels segmented as bone; and
          matching pixels that are segmented as bone to the region where the spinal cord should be based on bone features;
        locating rib bones of the patient by:
          identifying a first rib bone based on shape of the bone and spacing from a spine; and
          identifying successive rib bones based on a distance and angle formed relative to each previously identified rib; and
        generating vectors originating from the spinal cord to rib bones of the patient; and
      removing pixels segmented as not bone that are located within the location of the rib cage;
    calculate a volume of muscle based on remaining pixels segmented as not bone;

calculate a total muscle mass based on the volume of muscle;

provide the total muscle mass of the patient;

receive a measurement of creatinine levels of the patient;

calculate a glomerular filtration rate of the patient based on at least the total muscle mass of the patient and the measurement of creatinine levels of the patient; and provide the glomerular filtration rate.

17. The system of claim 16, wherein the glomerular filtration rate of the patient is further based on a patient's weight, age, race, and gender.

* * * * *